US006908899B2

(12) United States Patent
Smith

(10) Patent No.: US 6,908,899 B2
(45) Date of Patent: Jun. 21, 2005

(54) PRO-INFLAMMATORY FIBRINOPEPTIDE

(75) Inventor: Theresa H. Smith, Lebanon, CT (US)

(73) Assignee: U.S. Dept. of Veterans Affairs, Washington, DC (US)

( * ) Notice: Subject to any disclaimer, the term of this patent is extended or adjusted under 35 U.S.C. 154(b) by 411 days.

(21) Appl. No.: 09/931,009

(22) Filed: Aug. 17, 2001

(65) Prior Publication Data

US 2003/0109431 A1 Jun. 12, 2003

(51) Int. Cl.$^7$ .................. A61K 38/00; A61K 38/08
(52) U.S. Cl. .................. 514/17; 530/329; 530/330; 514/2
(58) Field of Search .................. 514/2, 18, 17; 530/329, 330

(56) References Cited

U.S. PATENT DOCUMENTS

| | | | |
|---|---|---|---|
| 4,816,449 A | 3/1989 | Hahn | |
| 5,061,786 A | 10/1991 | Burnier et al. | |
| 5,478,810 A | * 12/1995 | Stuber et al. | .................. 514/17 |
| 5,608,035 A | 3/1997 | Yanofsky et al. | |
| 5,629,293 A | 5/1997 | Undheim et al. | |
| 5,679,782 A | 10/1997 | Rosenberg et al. | |
| 5,719,064 A | 2/1998 | Scofield et al. | |
| 5,731,166 A | 3/1998 | Geczy et al. | |
| 5,767,234 A | 6/1998 | Yanofsky et al. | |
| 5,776,892 A | 7/1998 | Counts et al. | |
| 6,011,014 A | 1/2000 | Andersen et al. | |
| 6,030,940 A | 2/2000 | Rosenberg et al. | |
| 6,103,711 A | 8/2000 | Bemis et al. | |
| 6,126,939 A | 10/2000 | Eisenbach-Schwartz et al. | |
| 6,133,319 A | 10/2000 | Widdowson | |
| 6,147,096 A | 11/2000 | Dodd et al. | |
| 6,150,372 A | 11/2000 | Palanki et al. | |

OTHER PUBLICATIONS

Christine Masson–Bessiére et al., The Major Synovial Targets of the Rheumatoid Arthritis–Specific Antifilaggrin Autoantibodies Are Deiminated Forms of the α– and β–Chains of Fibrin, *The Journal of Immunology*, 2001, vol. 166: pp 4177–4184.
Xiufang Liu et al., Fibrin(ogen)–Induced Expression of ICAM–1 and Chemokines in Human Synovial Fibroblasts, *The Journal of Immunology*, 2000, vol. 165: pp 5255–5261.
Colvin RB, Johnson RA, Mihm MC, and Dvorak HF. *Role of the Clotting System in Cell–Mediated Hypersensitivity.* J Exp Med 1973, 138:686–698.
Accini L, Dixon FJ. *Degenerative Vascular Disease and Myocardial Infarction in Mice with Lupus–like Syndrome.* Am J. Pathol 1979, 96:477–492.
Wood RM, Bick MW. *The Effect of Heparin on the Ocular Tuberculin Reaction.* Arch Opthamol 1959, 61:709–711.
Cohen SB, Benacerraf B, McCluskey RT, Ovary Z. *Effects of Anticoagulants on Delayed Hypersensitivity Reaction.* J Immunol 1967, 98:351–358.

Colvin RB, Dvorak HF. *Role of the Clotting System in Cell–Mediated Hypersensitivity II. Kinetics of Fibrinogen/ fibrin Accumulation and Vascular Permeability Changes in Tuberculin and Cutaneous Basophil Hypersensitivity Reactions.* J Immunol 1975, 114:377–387.
Edwards RL, and Rickles FR. *Delayed Hypersensitivity in Man: Effects of Systemic Anticoagulation.* Science 1978, 200:541–543.
Colvin RB, Mosesson MW, Dvorak HF. *Delayed Type Hypersensitivity Skin Reactions in Congenital Afibrinogenemia Lack Fibrin Deposition and Induration.* J Clin Invest 1979, 63:1302–1306.
Malik AB, Johnson A, Tahamont MV. *Mechanisms of Lung Vascular Injury After Intravascular Coagulation.* Ann NY Acad Sci 1982, 384:213–234.
Kay AB, Pepper DS, McKenzie R. *The Identification of Fibrinopeptide B as a Chemotactic Agent Derived from Human Fibrinogen.* Br J Hematol 1974, 27:669–677.
Richardson DL, Pepper DS, Kay AB. *Chemotaxis for Human Monocytes by Fibrinogen Derived Peptides.* Br J Hematol 1976, 32:507–513.
Sueishi K, Nanno S, Tanaka K. *Permeability Enhancing and Chemotactic Activities of Lower Molecular Weight Degradation Products of Human Fibrinogen.* Thromb Haemost 1981, 45:90–94.
Rowland F, Donovan M, Gillies C, O'Rourke J, Kreutzer DL: *Fibrin: Mediator of In Vivo and In Vitro Injury and Inflammation.* Curr Eye Res 1985, 4:537–553.
Saxne T, Lecander I, Geborek P. *Plasminogen Activators and Plasminogen Activator Inhibitors in Synovial Fluid Difference Between Inflammatory Joint Disorders and Osteoarthritis.* J Rheumatol 1993, 20:91–96.
Kikuchi H, Tanaka S, Matsuo O. *Plasminogen Activator in Synovial Fluid from Patients with Rheumatoid Arthritis.* J Rheumatol 1987, 14:439–445.
Kummer JA, Abbink JJ, De Boer JP, Roem D, Nieuwenhuys EJ, Kamp AM, Swaak TJG, Hack CE. *Analysis of Intraarticular Fibrinolytic Pathways in Patients with Inflammatory and Noninflammatory Joint Diseases.* Arthritis Rheum 1992, 35:884–893.
Belch JJF, McArdle B, Madhok R. *Decreased Plasma Fibrinolysis in Patients with Rheumatoid Arthritis.* Ann Rheum Dis 1984, 43:774–777.
Dahlquist SR, Jonsson SW, Ranby M. *Fibrinolytic Components in Synovial Fluid of Destructive and Non–Destructive Arthritis.* Arthritis Rheum 1994, 37:S248.

(Continued)

Primary Examiner—Karen Cochrane Carlson
Assistant Examiner—Samuel W. Liu
(74) Attorney, Agent, or Firm—Dinesh Agarwal, P.C.

(57) ABSTRACT

A synthetic tetrapeptide having an amino acide sequence, Glycine-Proline-Arginine-Proline (GPRP) has pro-inflammatory effects on human fibroblastic cells, including synovial cells. An amide analog of GPRP is ineffective in inducing, or effective in causing a loss of, pro-inflammatory effects.

4 Claims, 5 Drawing Sheets

OTHER PUBLICATIONS

Herrick AL, Illingworth K, Blann A, Hollis S, Jayson MIV. *Von Willebrand Factor, Thromboxane, B–Thromboglobulin and Markers of Fibrinolysis in Primary Raynaud's Phenomenon and Systemic Sclerosis.* Arthritis Rheum 1994, 37:S259.

Qi J, Kreutzer DL, Piela–Smith TH. *Fibrin Induction of ICAM–1 Expression in Human Vascular Endothelial Cells.* J Immunol 1997, 158:1880–1886.

Kawasaki K, Hirase K, Masanori M, Tsuji T, Iwamoto, M. *Amino Acids and Peptides XVI. Synthesis of N–terminal Tetrapeptide Analogs of Fibrin a Chain and Their Inhibitory Effects on Fibronogen/fibrin Clotting.* 1992. Chem Pharm Bull 40:3253–3260.

Cliffton EE, Grossi CE. *The Rationale of Anticoagulants in the Treatment of Cancer.* J Med 1974, 5:107–113.

Peterson HI. *Fibrinolysis and Antifibrinolytic Drugs in the Growth and Spread of Tumors.* Cancer Treat Rev 1977, 4:213–217.

Zacharski LR, Henderson WG, Rickles FR, Forman WB, Cornell CJ Jr, Forcier RJ, Edwards R, Headley E, Kim SH, O'Donnell JR, O'Dell R, Tornyos K, Kwaan HC. *Effects of Warfarin on Survival in Small Cell Carcinoma of the Lung.* JAMA 1981, 245:831–835.

Bardos H, Juhasz A, Repassy G, Adany R. *Fibrin Deposition in Squamous Cell Carcinomas of the Larynx and Hypopharynx.* Thromb Haemost 1998, 80:767–772.

Laudano AP, Doolittle RF. *Studies on Synthetic Peptides That Bind to Fibrinogen and Prevent Fibrin Polymerization. Structural Requirements, Number of Binding Sites, and Species Differences.* 1980, Biochemistry 19:1013–1019.

Shreck R, Meier B, Manne D, Droge W, Bauerle PA. *Dithiocarbamate as Potent Inhibitors of Nuclear Factor κB in Intact Cells.* J Exp Med 1992, 175:1181–1194.

Lorenz H–M, Kalden JR. *Biologic Agents in the Treatment of Inflammatory Rheumatic Diseases.* 1999, Curr Opin Rheumatol 11:179–184.

Rothchild, BM, Thompson, LD, Pifer DD, Chesney CM. *Perturbation of Protease Inhibitors and Substrates in Inflammatory Arthritis.* Semin Thromb Hemostasis 1985, 11:394–404.

Belch JJF, Madhok R, McArdle B, McLaughlin K, Kluft C, Forbes CD, Sturrock RD. *The Effect of Increasing Fibrinolysis in Patients with Rheumatoid Arthritis: A Double Blind Study of Stanozolol.* Q J Med 1986, 58:19–27.

* cited by examiner

Ala Asp Ser Gly Glu Gly Asp Phe Leu Ala Glu Gly Gly Gly Val
                  5                       10                      15
Arg Gly Pro Arg Val Val Glu Arg His Gln Ser Ala Cys Lys Asp
                 20                       25                      30
Ser Asp Trp Pro Phe Cys Ser Asp Glu Asp Trp Asn Tyr Lys Cys
                 35                       40                      45
Pro Ser Gly Cys Arg Met Lys Gly Leu Ile Asp Glu Val Asn Gln
                 50                       55                      60
Asp Phe Thr Asn Arg Ile Asn Lys Leu Lys Asn Ser Leu Phe Glu
                 65                       70                      75
Tyr Gln Lys Asn Asn Lys Asp Ser His Ser Leu Thr Thr Asn Ile
                 80                       85                      90
Met Glu Ile Leu Arg Gly Asp Phe Ser Ser Ala Asn Asn Arg Asp
                 95                      100                     105
Asn Thr Tyr Asn Arg Val Ser Glu Asp Leu Arg Ser Arg Ile Glu
                110                      115                     120
Val Leu Lys Arg Lys Val Ile Glu Lys Val Gln His Ile Gln Leu
                125                      130                     135
Leu Gln Lys Asn Val Arg Ala Gln Leu Val Asp Met Lys Arg Leu
                140                      145                     150
Glu Val Asp Ile Asp Ile Lys Ile Arg Ser Cys Arg Gly Ser Cys
                155                      160                     165
Ser Arg Ala Leu Ala Arg Glu Val Asp Leu Lys Asp Tyr Glu Asp
                170                      175                     180
Gln Gln Lys Gln Leu Glu Gln Val Ile Ala Lys Asp Leu Leu Pro
                185                      190                     195
Ser Arg Asp Arg Gln His Leu Pro Leu Ile Lys Met Lys Pro Val
                200                      205                     210
Pro Asp Leu Val Pro Gly Asn Phe Lys Ser Gln Leu Gln Lys Val
                215                      220                     225
Pro Pro Glu Trp Lys Ala Leu Thr Asp Met Pro Gln Met Arg Met
                230                      235                     240

FIGURE 1A

Glu Leu Glu Arg Pro Gly Gly Asn Glu Ile Thr Arg Gly Gly Ser
                245                 250                 255
Thr Ser Tyr Gly Thr Gly Ser Glu Thr Glu Ser Pro Arg Asn Pro
                260                 265                 270
Ser Ser Ala Gly Ser Trp Asn Ser Gly Ser Ser Gly Pro Gly Ser
                275                 280                 285
Thr Gly Asn Arg Asn Pro Gly Ser Ser Gly Thr Gly Gly Thr Ala
                290                 295                 300
Thr Trp Lys Pro Gly Ser Ser Gly Pro Gly Ser Thr Gly Ser Trp
                305                 310                 315
Asn Ser Gly Ser Ser Gly Thr Gly Ser Thr Gly Asn Gln Asn Pro
                320                 325                 330
Gly Ser Pro Arg Pro Gly Ser Thr Gly Thr Trp Asn Pro Gly Ser
                335                 340                 345
Ser Glu Arg Gly Ser Ala Gly His Trp Thr Ser Glu Ser Ser Val
                350                 355                 360
Ser Gly Ser Thr Gly Gln Trp His Ser Glu Ser Gly Ser Phe Arg
                365                 370                 375
Pro Asp Ser Pro Gly Ser Gly Asn Ala Arg Pro Asn Asn Pro Asp
                380                 385                 390
Trp Gly Thr Phe Glu Glu Val Ser Gly Asn Val Ser Pro Gly Thr
                395                 400                 405
Arg Arg Glu Tyr His Thr Glu Lys Leu Val Thr Ser Lys Gly Asp
                410                 415                 420
Lys Glu Leu Arg Thr Gly Lys Glu Lys Val Thr Ser Gly Ser Thr
                425                 430                 435
Thr Thr Thr Arg Arg Ser Cys Ser Lys Thr Val Thr Lys Thr Val
                440                 445                 450
Ile Gly Pro Asp Gly His Lys Glu Val Thr Lys Glu Val Val Thr
                455                 460                 465
Ser Glu Asp Gly Ser Asp Cys Pro Glu Ala Met Asp Leu Gly Thr
                470                 475                 480

FIGURE 1B

Leu Ser Gly Ile Gly Thr Leu Asp Gly Phe Arg His Arg His Pro
             485                    490                    495
Asp Glu Ala Ala Phe Phe Asp Thr Ala Ser Thr Gly Lys Thr Phe
             500                    505                    510
Pro Gly Phe Phe Ser Pro Met Leu Gly Glu Phe Val Ser Glu Thr
             515                    520                    525
Glu Ser Arg Gly Ser Glu Ser Gly Ile Phe Thr Asn Thr Lys Glu
             530                    535                    540
Ser Ser Ser His His Pro Gly Ile Ala Glu Phe Pro Ser Arg Gly
             545                    550                    555
Lys Ser Ser Ser Tyr Ser Lys Gln Phe Thr Ser Ser Thr Ser Tyr
             560                    565                    570
Asn Arg Gly Asp Ser Thr Phe Glu Ser Lys Ser Tyr Lys Met Ala
             575                    580                    585
Asp Glu Ala Gly Ser Glu Ala Asp His Glu Gly Thr His Ser Thr
             590                    595                    600
Lys Arg Gly His Ala Lys Ser Arg Pro Val Arg Gly Ile His Thr
             605                    610                    615
Ser Pho Leu Gly Lys
             620

FIGURE 1C

Ala Asp Ser Gly Glu Gly Asp Phe Leu Ala Glu Gly Gly Gly Val Arg | Gly
        5              10                    15
Pro Arg Val Val Glu Arg His
    20

|◄─────────── FIBRINOPEPTIDE A ───────────►|

FIGURE 2

Gly Pro Arg Val
 17          20

FIGURE 3

Gly Pro Arg Pro

FIGURE 4

SEQUENCE LISTING

```
<160> NUMBER OF SEQ ID NOS: 4

<210> SEQ ID NO 1
<211> LENGTH: 620
<212> TYPE: PRT
<213> ORGANISM: Homo sapiens
<220> FEATURE:

<400> SEQUENCE: 1

Ala Asp Ser Gly Glu Gly Asp Phe Leu Ala Glu Gly Gly Gly Val
                5                  10                  15

Arg Gly Pro Arg Val Val Glu Arg His Gln Ser Ala Cys Lys Asp
             20                  25                  30

Ser Asp Trp Pro Phe Cys Ser Asp Glu Asp Trp Asn Tyr Lys Cys
             35                  40                  45

Pro Ser Gly Cys Arg Met Lys Gly Leu Ile Asp Glu Val Asn Gln
             50                  55                  60
```

-continued

```
Asp Phe Thr Asn Arg Ile Asn Lys Leu Lys Asn Ser Leu Phe Glu
             65                  70                  75

Tyr Gln Lys Asn Asn Lys Asp Ser His Ser Leu Thr Thr Asn Ile
             80                  85                  90

Met Glu Ile Leu Arg Gly Asp Phe Ser Ser Ala Asn Asn Arg Asp
             95                 100                 105

Asn Thr Tyr Asn Arg Val Ser Glu Asp Leu Arg Ser Arg Ile Glu
            110                 115                 120

Val Leu Lys Arg Lys Val Ile Glu Lys Val Gln His Ile Gln Leu
            125                 130                 135

Leu Gln Lys Asn Val Arg Ala Gln Leu Val Asp Met Lys Arg Leu
            140                 145                 150

Glu Val Asp Ile Asp Ile Lys Ile Arg Ser Cys Arg Gly Ser Cys
            155                 160                 165

Ser Arg Ala Leu Ala Arg Glu Val Asp Leu Lys Asp Tyr Glu Asp
            170                 175                 180

Gln Gln Lys Gln Leu Glu Gln Val Ile Ala Lys Asp Leu Leu Pro
            185                 190                 195

Ser Arg Asp Arg Gln His Leu Pro Leu Ile Lys Met Lys Pro Val
            200                 205                 210

Pro Asp Leu Val Pro Gly Asn Phe Lys Ser Gln Leu Gln Lys Val
            215                 220                 225

Pro Pro Glu Trp Lys Ala Leu Thr Asp Met Pro Gln Met Arg Met
            230                 235                 240

Glu Leu Glu Arg Pro Gly Gly Asn Glu Ile Thr Arg Gly Gly Ser
            245                 250                 255

Thr Ser Tyr Gly Thr Gly Ser Glu Thr Glu Ser Pro Arg Asn Pro
            260                 265                 270

Ser Ser Ala Gly Ser Trp Asn Ser Gly Ser Ser Gly Pro Gly Ser
            275                 280                 285

Thr Gly Asn Arg Asn Pro Gly Ser Ser Gly Thr Gly Gly Thr Ala
            290                 295                 300

Thr Trp Lys Pro Gly Ser Ser Gly Pro Gly Ser Thr Gly Ser Trp
            305                 310                 315

Asn Ser Gly Ser Ser Gly Thr Gly Ser Thr Gly Asn Gln Asn Pro
            320                 325                 330

Gly Ser Pro Arg Pro Gly Ser Thr Gly Thr Trp Asn Pro Gly Ser
            335                 340                 345

Ser Glu Arg Gly Ser Ala Gly His Trp Thr Ser Glu Ser Ser Val
            350                 355                 360

Ser Gly Ser Thr Gly Gln Trp His Ser Glu Ser Gly Ser Phe Arg
            365                 370                 375

Pro Asp Ser Pro Gly Ser Gly Asn Ala Arg Pro Asn Asn Pro Asp
            380                 385                 390

Trp Gly Thr Phe Glu Glu Val Ser Gly Asn Val Ser Pro Gly Thr
            395                 400                 405

Arg Arg Glu Tyr His Thr Glu Lys Leu Val Thr Ser Lys Gly Asp
            410                 415                 420

Lys Glu Leu Arg Thr Gly Lys Glu Lys Val Thr Ser Gly Ser Thr
            425                 430                 435

Thr Thr Thr Arg Arg Ser Cys Ser Lys Thr Val Thr Lys Thr Val
            440                 445                 450
```

-continued

```
Ile Gly Pro Asp Gly His Lys Glu Val Thr Lys Glu Val Val Thr
            455                 460                 465

Ser Glu Asp Gly Ser Asp Cys Pro Glu Ala Met Asp Leu Gly Thr
            470                 475                 480

Leu Ser Gly Ile Gly Thr Leu Asp Gly Phe Arg His Arg His Pro
            485                 490                 495

Asp Glu Ala Ala Phe Phe Asp Thr Ala Ser Thr Gly Lys Thr Phe
            500                 505                 510

Pro Gly Phe Phe Ser Pro Met Leu Gly Glu Phe Val Ser Glu Thr
            515                 520                 525

Glu Ser Arg Gly Ser Glu Ser Gly Ile Phe Thr Asn Thr Lys Glu
            530                 535                 540

Ser Ser Ser His His Pro Gly Ile Ala Glu Phe Pro Ser Arg Gly
            545                 550                 555

Lys Ser Ser Ser Tyr Ser Lys Gln Phe Thr Ser Ser Thr Ser Tyr
            560                 565                 570

Asn Arg Gly Asp Ser Thr Phe Glu Ser Lys Ser Tyr Lys Met Ala
            575                 580                 585

Asp Glu Ala Gly Ser Glu Ala Asp His Glu Gly Thr His Ser Thr
            590                 595                 600

Lys Arg Gly His Ala Lys Ser Arg Pro Val Arg Gly Ile His Thr
            605                 610                 615

Ser Pro Leu Gly Lys
            620

<210> SEQ ID NO 2
<211> LENGTH: 4
<212> TYPE: PRT
<213> ORGANISM: Artificial Sequence
<220> FEATURE:
<223> OTHER INFORMATION: Unknown. Obtained from a commercial source.

<400> SEQUENCE: 2

Gly Pro Arg Pro

<210> SEQ ID NO 3
<211> LENGTH: 4
<212> TYPE: PRT
<213> ORGANISM: Artificial Sequence
<220> FEATURE:
<223> OTHER INFORMATION: Unknown. Obtained from a commercial source.

<400> SEQUENCE: 3

Lys Arg Glu Glu

<210> SEQ ID NO 4
<211> LENGTH: 12
<212> TYPE: PRT
<213> ORGANISM: Artificial Sequence
<220> FEATURE:
<223> OTHER INFORMATION: Unknown. Obtained from a commercial source.

<400> SEQUENCE: 4

Gly Pro Arg Val Val Glu Arg His Gln Ser Ala Cys
                 5                  10
```

PRO-INFLAMMATORY FIBRINOPEPTIDE

REFERENCE TO SEQUENCE LISTING

The present application incorporates by reference SEQ ID NO: 1, SEQ ID NO: 2, SEQ ID NO: 3 and SEQ ID NO: 4 provided herewith on a diskette, created on Jan. 11, 2005 and containing 5,979 bytes. The information recorded on the diskette is identical to the written sequence listing provided herein.

FIELD AND HISTORICAL BACKGROUND OF THE INVENTION

The present invention is directed to the treatment of rheumatoid arthritis (RA), and more particularly to a synthetic peptide sequence that has been discovered to induce pro-inflammatory effects in human synovial cells.

In the clotting of blood, a large protein dissolved in the plasma, known as "fibrinogen", is cut-up by an enzyme into an insoluble protein known as "fibrin", and other smaller fragments. Fibrin polymerizes to form the tough protein clot involved in blood coagulation. In addition to blood clots, polymerized fibrin is found in many inflamed, injured tissues, some of which are not the site of gross bleeding. Specifically, fibrin is found deposited on the inflamed joint surfaces of rheumatoid arthritis patients, in association with certain other inflammatory diseases, and with certain cancers. In rheumatoid arthritis, the amount of fibrin in the synovial membranes of the inflamed joints was found in the late 1970's to correlate with the severity of the disease, although the exact mechanism behind this relationship was not known.

Fibrin deposition, long recognized as a hallmark of acute and chronic inflammatory processes, has been localized within various inflamed tissues by histological, ultrastructural, and immunoflourescent procedures (References 1 and 2). A common theme of numerous studies is that fibrin plays an active role in the induction of inflammation (References 3–8), and demonstrate that fibrin can function beyond its classic role as a hemostatic plug or temporary matrix in response to injury. However, only recently has the direct impact of fibrin metabolism on the inflammatory process been seriously investigated, and specific roles assigned to fibrin or its products as mediators of the process (References 9–12). Although fibrin is abundantly present in many inflamed tissues rich in fibroblastic cells, no significant data on fibrin(ogen) metabolite induced gene expression by fibroblasts (FB) have been published.

Previously, research has focused on the cytokine pathways of adhesion molecule induction and adhesion molecule-related mechanisms thought to be important in connective tissue diseases, such as Rheumatoid Arthritis (RA) and Scleroderma (SD). In these diseases, evidence for altered fibrinolysis has been demonstrated, for example, in plasma and synovial fluids in RA (References 13–14). It has long been recognized that in most inflamed joints, the coagulation system is activated leading to the local generation of fibrin (Reference 15), and it has been hypothesized that the local fibrin deposition in arthritic joints could promote inflammation and destruction (Reference 16). Indeed, animal studies in which fibrin is implanted locally within joints induces a reaction that resembles human RA (Reference 28). Currently, studies are attempting to correlate associations between synovial fibrinolysis and levels of joint destruction in RA (Reference 17) and fibrinolysis with the severity of the disease state in SD (Reference 18), two diseases in which resident fibroblasts (FB) appear to play crucial roles. However, direct effects of fibrin on FB have not been previously examined with regard to the generation/maintenance of inflammation within connective tissue. Because of the universal nature of fibrin deposition in injured and inflamed tissue, determining the mediators, mechanisms and consequences of fibrin-induced activation of FB is important in not only understanding the pathways, but developing important new insights into the regulation of inflammation in connective tissue. Previous research pursued this avenue of investigation and it was found that fibrin clots could induce adhesion molecule expression in human synovial fibroblasts.

The treatment of RA has two clinical objectives: symptomatic reduction of pain and inflammation and prevention of joint damage. Scientists are experimenting with new drugs and biological agents that selectively block certain immune system activities associated with inflammation. Recent studies suggest that these represent promising approaches to treatment.

Current therapy for RA consists of non-steroidal anti-inflammatory drugs (NSAIDs), and as the disease progresses, oral steroids. Finally, disease modifying anti-rheumatic drugs (DMARDs) are added to the course of therapy.

It should be noted that no currently available agent truly improves the outcome of RA. DMARDs, such as methotrexate and sulfasalazine interfere with the inflammatory process but do not reverse or halt the progression of RA over long-term therapy. Moreover, while these agents initially work for most patients, both DMARDs and NSAIDs can cause serious side effects. And, while initial clinical response to DMARDs occurs in about 70–80% of patients, the effectiveness diminishes to approximately 20% of patients over time. It is estimated that 10% of the 2.5 million RA patients in the United States do not respond to current therapies.

Development of novel treatments for RA has been facilitated by two important factors: (1) progress in the understanding of the immunopathogenesis of RA, and (2) developments in biotechnology.

OBJECTS AND SUMMARY OF THE INVENTION

The principal object of the present invention is to provide a peptide (or fibrinopeptide or tetrapeptide) that has pro-inflammatory effects on human synovial cells and little to no effects on human foreskin fibroblasts. The peptide bears homology with a natural sequence found in the human fibrin molecule formed during fibrinogenesis, and is a potent inducer of several pro-inflammatory mediators in human synovial cells.

The peptide of the invention is believed to play a role in inflammatory lung diseases in which fibrin deposition is also known to occur. My research has proven that human lung fibroblastic cells are also responsive to the fibrinopeptide, and under its influence, will express selective pro-inflammatory molecules on the cell surface and will secrete pro-inflammatory mediators, such as cytokines and chemical attractants for immune cells.

Another object of the present invention is to provide a peptide which could be used as a valuable tool in exploring the efficacy of clinical treatments in RA and other diseases in which fibrin is suspected of playing an inflammatory role. For instance, if one wishes to design new anti-inflammatory compounds to address or subdue this new pathway of inflammation, or to evaluate the effectiveness of existing compounds or treatments on fibrin-induced inflammation, the four amino acid peptide of the invention is a cleaner system of cell activation than using the entire fibrin molecule. In in vivo animal studies (required testing), intact fibrin would be expected to undergo additional cleavage and folding reactions within tissues and many of the resulting fragments are known to have myriad effects on different cell types which would make interpretation of results difficult. The use of the isolated fibrinopeptide of the invention eliminates this difficulty.

Yet another object of the present invention is to provide a peptide which has the significant advantage in that it can be used to identify, isolate and clone the cell receptor to which it binds. This would likely lead to significant commercial value.

An additional object of the present invention is to provide an analog of the peptide which is ineffective in inducing, or effective in causing a loss of, pro-inflammatory effects. This is believed to be particularly useful in the treatment or prevention of inflammation of a synovial joint, and related disorders, such as rheumatoid arthritis.

Yet an additional object of the present invention is to provide all analogs, mutants, fragments, derivatives, functional homologs and other variants of the peptide of the invention.

In summary, the present invention is based on the discovery that a synthetic four amino acid peptide has pro-inflammatory effects on synovial cells. The peptide of the invention has an amino acid sequence of Glycine-Proline-Arginine-Proline. An amide analog of the peptide has been found to be ineffective in inducing, or effective in causing a loss of, pro-inflammatory effects.

BRIEF DESCRIPTION OF THE DRAWINGS

The above and other objects, novel features and advantages of the present invention will become apparent from the following detailed description of the invention, as illustrated in the drawings, in which:

FIGS. 1(A–C) illustrates an amino acid sequence of human fibrinogen Aα chain set forth in SEQ ID NO:1;

FIG. 2 illustrates cleavage of fibrinopeptide A by thrombin;

FIG. 3 illustrates the natural sequence of amino acids 17 through 20 of the Aα chain of fibrinogen;

FIG. 4 illustrates the amino acid sequence of the peptide of the invention set forth in SEQ ID NO: 2.

DETAILED DESCRIPTION OF THE INVENTION

Figure 5:
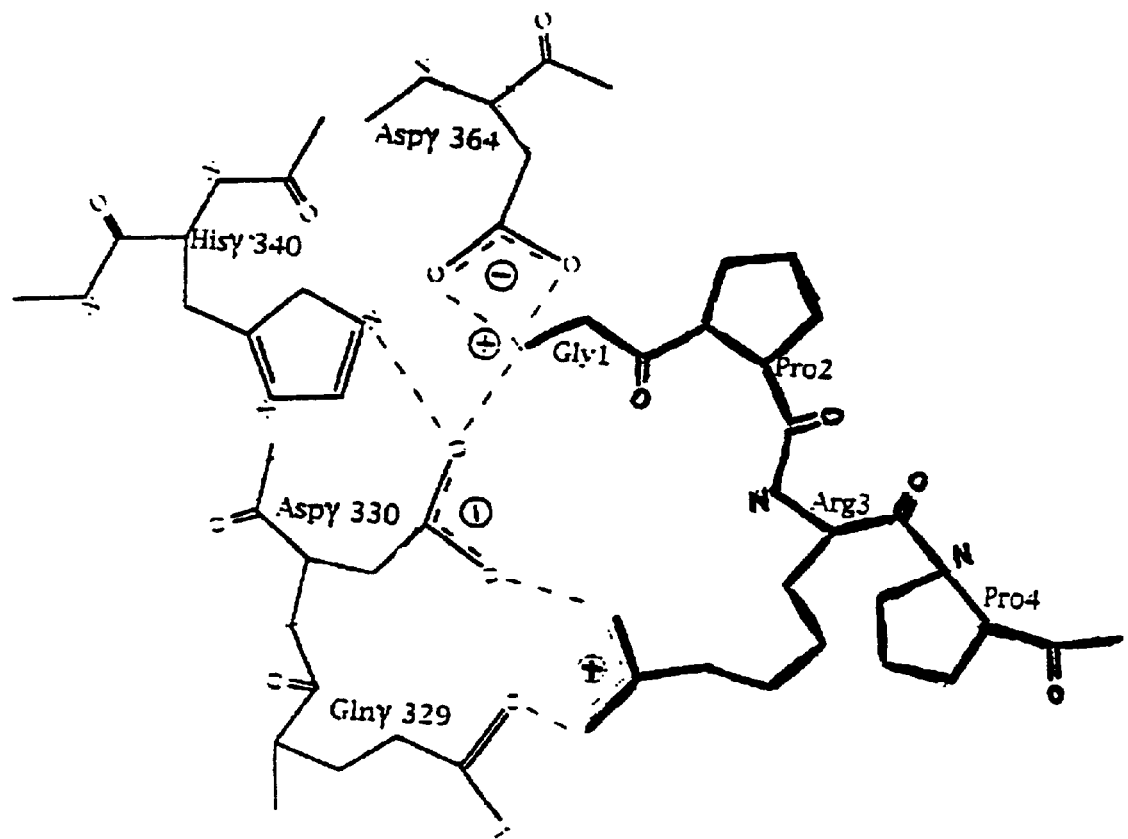
FIG. 5 is a two-dimensional diagram based on X-ray structure illustrating hydrogen bonds and electrostatic interactions between the GPRP(SEQ ID NO:2) knob and the γ-chain hole.

The amino acid sequence of the pro-inflammatory peptide of the invention is Gly-Pro-Arg-Pro (GPRP) (SEQ ID NO:2). This sequence is related to amino acids 17 through 20 of the A/alpha chains of fibrinogen (FIG. 1). Amino acids 1 through 16 of the A/alpha chains are cleaved-off by thrombin or thrombin-like proteases in vivo and this now separated peptide is known as Fibrinopeptide A. Cleavage of Fibrinopeptide A by thrombin is the initial cleavage in the formation of fibrin clots from its precursor, fibrinogen (see FIG. 2). This cleavage exposes new amino-termini of the A/alpha chains (beginning with amino acid number 17) with the leading sequence Gly-Pro-Arg. These newly exposed sequences, which are centrally located in a spatial model of fibrinogen have been referred to as "knobs", and are able to bind to complementary "holes" in the gamma chains of the same or different fibrinogen molecules and thus facilitate the crosslinking of fibrin(ogen) into a meshwork, or clot (see FIG. 5). I believe that there exists another receptor-like "hole" on the surface of human synovial cells, through which the "knobs" can mediate pro-inflammatory effects.

Synthetic peptides modeled after these "knobs" are able to inhibit fibrin polymerization by covering up the "holes" on the gamma chains and are commercially available. The natural sequence of the new amino terminus following Fibrinopeptide A cleavage is tripeptide consisting of Gly-Pro-Arg or tetrapeptide comprising core sequence Gly-Pro-Arg, and this peptide functions well as a polymerization inhibitor (see page 1015 of Laudano et al. reference, i.e., Reference 25. It was found that the modified peptide Gly-Pro-Arg-Pro (SEQ ID NO:2) was an even more potent inhibitor of polymerization, although the reason why is not understood and is hypothesized to be due to steric constraints (rigidity) imposed by the terminal proline. Many studies of fibrinogen polymerization make use of such synthetic peptides. I first used a commercial GPRP to inhibit fibrin polymerization in studies of fibrin co-culture with endothelial cells and have published our results (Reference 19). I found GPRP (SEQ ID NO:2) to be a good inhibitor of fibrin polymerization yet had no direct effects itself on endothelial cells. I also found GPRP to have low to no effects on other cell types, such as foreskin fibroblasts.

I derived several primary cell lines from the synovium of RA and osteoarthritis (OA) patients. I wanted to examine the effects, if any, of polymerized fibrin on synovial fibroblasts in vitro, to mimic the environment found in vivo in a rheumatoid joint. I was surprised to find that the inclusion of GPRP (SEQ ID NO:2) along with fibrinogen (to inhibit polymerization) did not abrogate my initial findings of increased ICAM-1 (Intercellular Adhesion Molecule-1) expression (caused by exposure to fibrin clots) by the synovial FB. ICAM-1 is considered to be such a key component in the inflammation of the rheumatoid joint, that RA therapeutic trials have been based on the inactivation of ICAM-1 alone. Indeed, I found that the GPRP (SEQ ID NO:2) peptide alone was able to induce ICAM-1 expression by the synovial fibroblasts as measured both by ELISA and flow cytometry. By flow cytometry, GPRP (SEQ ID NO:2) peptide increased ICAM-1 expression in two ways: 1) increasing the percentage of cells expressing ICAM-1, and 2) increasing the amount of surface ICAM-1 per cell. I conducted experiments with more than seven different RA fibroblast lines and obtained consistently increased expression of ICAM-1 induced by GPRP (SEQ ID NO:2) with all lines. My experience is that GPRP is able to reliably induce the adhesion molecule ICAM-1 about as well as any cytokine. The effects of GPRP (SEQ ID NO:2) on ICAM-1 induction are dose-dependent. A significant induction at 1.0, 0.5, and 0.1 mg/ml was observed. Induction at 0.01 mg/ml was found not to be significant.

Table 1 illustrates an experiment using GPRP (SEQ ID NO:2) to increase ICAM-1 expression on different RA synovial cell lines assayed by flow cytometry, and compares those results with the failure of GPRP (SEQ ID NO:2) to induce ICAM-1 on human foreskin fibroblasts.

TABLE 1

FLOW CYTOMETRY ANALYSIS OF ICAM-1 EXPRESSION ON HUMAN FIBROBLASTS
Fibroblasts were incubated with culture medium (control) or medium containing fibrin clot (0.6 mg/ml) or the tetrapeptide of the invention, GPRP (SEQ ID NO:2) (1 mg/ml). Fibroblasts were washed and incubated with saturating concentrations of anti-ICAM-1 antibody followed by staining with FITC-conjugated goat anti-mouse IgG. Positive regions were set to exclude 97% of non-specifically stained cells, determined using an irrelevant primary antibody.

| Cell Line | % positive | MFC |
|---|---|---|
| RA line 9 control | 43.4 | 1.09 |
| RA line 9 + fibrin | 68.5 | 2.17 |
| RA line 9 + GPRP | 80.1 | 3.62 |
| RA line 4 control | 45.5 | 1.47 |
| RA line 4 + fibrin | 72.0 | 1.53 |
| RA line 4 + GPRP | 87.0 | 2.73 |
| RA line 5 control | 33.3 | 1.09 |
| RA line 5 + GPRP | 74.5 | 2.00 |
| RA line 6 control | 86.3 | 2.41 |
| RA line 6 + GPRP | 95.0 | 9.19 |
| Foreskin fibroblasts control | 85.6 | 1.89 |
| Foreskin fibroblasts + GPRP | 86.7 | 2.26 |

Table 2 illustrates an experiment using GPRP (SEQ ID NO:2) to increase ICAM-1 in different RA synovial lines assayed by ELISA and compares those results with the failure of GPRP (SEQ ID NO:2) to induce ICAM-1 on human foreskin fibroblasts.

TABLE 2

ICAM-1 EXPRESSION BY ELISA
Synovial or foreskin fibroblasts were incubated overnight with either control medium, fibrin clots (0.6 mg/ml), or GPRP (SEQ ID NO:2) (1 mg/ml). Cell-ELISA was performed the following morning for ICAM-1 expression on the cell surface. Optical Density was read at 492 nm. Results are expressed as mean ± standard deviation for triplicate determinations.

| Cell Line | O.D. 492 |
|---|---|
| RA line 9 control | 0.44 ± .11 |
| RA line 9 + fibrin | 1.15 + .04 |
| RA line 9 + GPRP | 0.98 ± .15 |
| RA line 4 control | 0.48 ± .05 |
| RA line 4 + fibrin | 1.19 ± .14 |
| RA line 4 + GPRP | 1.04 ± .02 |
| RA line 5 control | 0.59 ± .02 |
| RA line 5 + fibrin | 1.16 ± .06 |
| RA line 5 + GPRP | 1.10 ± .03 |
| Foreskin fibroblasts control | 0.46 ± .06 |
| Foreskin fibroblasts + fibrin | 0.59 ± .13 |
| Foreskin fibroblasts + GPRP | 0.55 ± .05 |
| Foreskin fibroblasts + interferon γ (200 U/ml) (positive control for foreskin fibroblasts) | 1.57 ± .13 |

As can be observed, the ability of GPRP (SEQ ID NO:2) to induce ICAM-1 on synovial fibroblasts is as good as whole fibrin clot.

Table 3 shows GPRP induction of IL-6 (measured by ELISA). Table 4 shows a dose-dependent increase in ICAM-1 expression on synovial FB by GPRP (SEQ ID NO:2).

TABLE 3

GPRP INDUCTION OF IL-6 - MEASURED BY ELISA
Synovial or foreskin fibroblasts were incubated overnight with and without GPRP (SEQ ID NO:2). An IL-6 ELISA was performed the following day on the cell supernatants.

| Cell Line | Control pg/ml | GPRP pg/ml | INCREASE |
|---|---|---|---|
| RA #1 | 1600 | 2400 | 1.50X |
| RA #11 | 275 | 1700 | 6.18X |
| RA #16 | 3000 | 11100 | 3.70X |
| RA #18 | 490 | 940 | 1.90X |
| Foreskin Fibroblasts | 255 | 215 | — |

TABLE 4

GPRP INCREASES ICAM-1 ON SYNOVIAL FIBROBLASTS IN A DOSE DEPENDENT MANNER
Synovial and Foreskin fibroblasts (FF) were incubated overnight with varying concentrations of GPRP (SEQ ID NO:2). Cell ELISAS were performed the following day for ICAM-1 expression on the cell surface.

| | RA#11 OD 492 | RA#12 OD 492 | FF-#1 OD 492 | FF-#2 OD 492 |
|---|---|---|---|---|
| Control | .25 ± .02 | 0.53 ± .05 | 0.95 ± .01 | .72 ± .04 |
| GPRP 1.00 mg/ml | .59 ± .05 | 1.42 ± .08 | 1.02 ± .01 | .78 ± .04 |
| 0.30 | .46 ± .05 | 1.09 ± .06 | 0.99 ± .01 | .72 ± .03 |
| 0.10 | .37 ± 0 | 0.76 ± .03 | 0.92 ± .02 | .72 ± .02 |
| .030 | .31 ± .02 | 0.62 ± .03 | 0.94 ± .05 | .70 ± .02 |
| .010 | .24 ± .05 | 0.57 ± .02 | 0.93 ± .03 | .71 ± .02 |
| .003 | .25 ± .03 | 0.53 ± .01 | 0.95 ± .06 | .71 ± .04 |
| .001 | .24 ± .05 | 0.51 ± .01 | 0.92 ± .01 | .69 ± .02 |

I also assayed several lines for V-CAM-1 expression, and found that about 50% of the lines tested upregulated V-CAM-1 expression in response to the peptide. I also found that VCAM-1 induction is not as robust as ICAM-1.

I have confirmed an upregulation of functional adhesion molecules by GPRP (SEQ ID NO:2) using a human in vitro T cell adhesion assay (see Table 5 below).

TABLE 5

GPRP INDUCES T CELL ADHESION
Synovial (RA and OA derived) or foreskin fibroblast cells were incubated with culture medium (control) or medium containing IL-1 beta (1 ng/ml, an inducer of ICAM-1) or GPRP (SEQ ID NO:2) (1.0 and 0.1 mg/ml) overnight. Cells were washed and 100 ul of fresh purified human T cells were added for one hour and non-adherent T cells were removed by washing. Adherent T cells (known to be adherent predominantly via ICAM-1 interaction with T-cell LFA-1) were counted after the cultures had been air dried and stained with 1% methylene blue. Results shown are T cell numbers ± standard deviations for triplicate wells counted using an ocular grid.

| Cell Line | Control | IL-1 | GPRP (1 mg/ml) | GPRP (0.1 mg/ml) |
|---|---|---|---|---|
| RA line 7 | 80 ± 8 | 116 ± 14 | 153 ± 54 | 184 ± 58 |
| RA line 8 | 29 ± 2 | 58 ± 21 | 97 ± 10 | 99 ± 18 |
| OA line 15 | 35 ± 6 | 66 ± 19 | 113 ± 44 | 92 ± 27 |
| Foreskin line | 47 ± 10 | 94 ± 16 | 54 ± 11 | 51 ± 3 |

One consideration in evaluating the effects of any substance on my collection of RA synovial cell lines, is that the synovial tissues I used were collected sequentially as the patient surgeries were scheduled. Therefore, I had no knowledge of the patients' disease history, or what medications they might have been taking or for how long.

Another effect of the peptide of the invention on synovial FB, is the induction of the chemotactic cytokines IL-8 and GRO-alpha, each of which is intimately involved in the recruitment of lymphocytes into inflamed tissues. I used commercial ELISA kits to assay cell culture supernatants of RA fibroblasts that were cultured for both 24 and 48 hours with or without peptide. RA Line 1 increased its production of IL-8 12.6-fold at twenty-four hours and fifteen-fold at forty-eight hours. RA Line 2 behaved similarly with ten-fold increases at both twenty-four and forty-eight hours. For comparison, monocytes, considered to be excessive IL-8 secreters, increase IL-8 production approximately three-fold when stimulated with phytohemagglutinin (PHA). It is believed that a technical error in the absorbance readings only of our GRO-alpha assay may have resulted in a very significant underestimation of the amount of GRO-alpha secreted in response to peptide. However, in a visual observation of developed ELISA plates, the fold increase was at least as much as was seen for IL-8 and probably is greater. Using foreskin FB as control cells, I accurately measured only a 1.2 fold increase in GRO-alpha secretion in response to the peptide both at twenty-four and forty-eight hours. I believe that not only does GPRP (SEQ ID NO:2) participate in the chemotactic recruitment of lymphocytes via induction of IL-8 and GRO-alpha, but it gives the lymphocytes a place to "park" once they arrive via the simultaneous induction of adhesion molecules such as ICAM-1 and VCAM-1.

Table 6 presents our ELISA results for the chemotactic cytokines IL-8 and GRO-alpha.

TABLE 6

GPRP INDUCTION OF CHEMOKINE SECRETION
FROM HUMAN SYNOVIAL FIBROBLASTS
Synovial or foreskin fibroblasts were incubated with control medium or
medium containing 1 mg/ml GPRP (SEQ ID NO:2) for 24 and 48 hours.
Cell culture supernatants were tested by commercial ELISA kits for the
chemokines IL-8 and GRO- alpha (R & D Systems, Minneapolis, MN).
All samples were additionally tested for Interferon γ secretion. All
supernatants were negative for Interferon γ secretion.

| | IL-8 (pg/ml) | | |
|---|---|---|---|
| Cell Line | Control | 24 hr | 48 hr |
| RA line 1 | 1260 | 16,000 | |
| RA line 1 | 1140 | | 17,500 |
| RA line 4 | 900 | 9,000 | |
| RA line 4 | 680 | | 6,800 |
| Foreskin fibroblasts | 400 | 1,840 | |
| Foreskin fibroblasts | 260 | | 1,200 |

| | GRO-alpha | |
|---|---|---|
| Cell Line | GRO-alpha pg/ml | Fold Increase |
| RA line 7 Control | 55 | |
| Fibrinogen | 8000 | 145X |
| RA line 8 Control | 400 | |
| GPRP | 8500 | 21X |
| Foreskin fibroblasts Control | 380 | 1.2X |
| GPRP | 470 | |

In another experiment using RT-PCR, it was found that synovial cells exposed to GPRP (SEQ ID NO:2) had significantly more IL-6 gene expression than controls. IL-6 has been demonstrated to be both a chemoattractant and pro-inflammatory cytokine in RA.

The GPRP (SEQ ID NO:2) peptide of the invention is believed to induce gene expression of ICAM-1 through its stimulation of the intracellular signal NF-kappaB which regulates the intensity of gene transcription. NF-kappaB activation is already well known to affect a broad array of immediate-early gene products, such as TNF, interleukins, chemokines and colony stimulating factors; genes that are tightly regulated during inflammation and wound healing. Inclusion of the specific inhibitor of NF-kappaB, pyrrolidinedithio-carbamate (PDTC), stopped the entire increase in ICAM-1 expression induced not only by Interleukin-1 (as expected), but also by the GPRP (SEQ ID NO:2) peptide. PDTC is an anti-oxidant that prevents NF-kappaB activation and its translocation to the nucleus (Reference 26). As NF-kappaB is also known to be involved in IL-8 transcription, it is expected that PDTC would also inhibit the IL-8 secretion induced by GPRP (SEQ ID NO:2).

Table 7 shows the inhibitory results of PTDC on the ability of GPRP (SEQ ID NO:2) to induce ICAM-1.

TABLE 7

PDTC INHIBITS IL-1 AND GPRP INDUCTION
OF ICAM-1 IN HUMAN SYNOVIAL CELLS
Cells were pre-incubated with PDTC for 1.5 hours before the addition of
IL-1 (positive control) or GPRP (SEQ ID NO:2) overnight. ELISA assay
for ICAM-1 was performed the following morning. Results are presented
as O.D. 492 ± standard deviation for triplicate determinations.

| | RA line 6 | RA line 5 | OA line 8 | OA line 2 |
|---|---|---|---|---|
| Control | 0.66 ± .03 | 0.85 ± .02 | 0.53 ± .03 | 0.69 ± .02 |
| IL-1 | 1.80 ± .04 | 1.88 ± .05 | 1.51 ± .05 | 1.60 ± .03 |
| IL-1 + PDTC | 0.70 ± .06 | 0.85 ± .07 | 0.60 ± .02 | 0.57 ± .01 |
| GPRP | 1.67 ± .06 | 1.83 ± .08 | 1.30 ± .09 | 1.66 ± .05 |
| GPRP + PDTC | 0.61 ± .02 | 0.75 ± .09 | 0.60 ± .02 | 0.65 ± .02 |
| PDTC alone | 0.61 ± .02 | 0.75 ± .06 | 0.55 ± .04 | 0.65 ± .03 |

Most modifications of the GPRP (SEQ ID NO:2) sequence (amino acid substitutions) are not effective polymerization inhibitors. For example, changing Gly1 to anything else destroys its inhibitory action as there appears to be no extra "room" for a side chain in the gamma chain "hole" into which it must fit. However, as noted below, amino acid Pro4 functions differently. Actually, Pro4 is not essential for activity, as Gly-Pro-Arg alone can inhibit fibrinogen polymerization, although inhibition is much more effective when Pro4 is included.

Changing the carboxyl group at the end of Pro4 to an amide group (OH to NH2) has been found to be approximately three and one-half times more effective at inhibiting polymerization as the original H-Gly-Pro-Arg-Pro-OH (SEQ ID NO:2) (Reference 20). Interestingly, when I substituted the amide analog of GPRP (SEQ ID NO:2), it was totally ineffective at inducing ICAM-1 in synovial fibroblasts. Although it is not yet shown that the amide form of GPRP (SEQ ID NO:2) still binds to the synovial cell receptor, it is unlikely that this change in the number four position would compromise binding ability. Further research is contemplated in using the amide analog of the peptide of the invention to determine if other pro-inflammatory responses of the synovial FB are also prevented.

Table 8 contains data comparing the activities of GPRP-OH (SEQ ID NO:2) and GPRP-NH2(SEQ ID NO:2). This Table also contains data showing that synovial cell incubation with other, coagulation-related peptides (Fibrinopeptides A and B, and an amino acid sequence which prevents platelet aggregation by binding to the fibrinogen receptor) have no effect on ICAM-1 induction.

TABLE 8

AMIDE FORM OF GPRP IS INEFFECTIVE AS AN INDUCER
OF ICAM-1 ON HUMAN SYNOVIAL FIBROBLASTS.

Synovial cells from patients with rheumatoid arthritis (RA), osteoarthritis
(OA) or foreskin fibroblasts were incubated overnight with culture
medium (control), or culture medium containing one of the following: 1)
IL-1 (0.5 ng/ml), 2) GPRP (1 mg/ml), 3) GPRP-amide (1 mg/ml), 4)
fibrinogen receptor peptide N-acetyl-Pen-Arg-Gly-Asp-Cys, (0.1 mg/ml,
related control peptide), or 5) Fibrinopeptides A and B, (FPA, FPB,
$10^{-4}$ M each). ICAM-1 was determined by ELISA and results are
presented as O.D. 492 ± standard deviation of triplicate determinations.

|                   | RA line 1     | RA line 2    | OA line      | Foreskin line |
|-------------------|---------------|--------------|--------------|---------------|
| Control           | 0.64 ± .02    | 0.43 ± .003  | 0.47 ± .04   | 0.74 ± .04    |
| IL-1 (pos control)| 1.74 ± .08    | 1.18 ± .03   | 1.36 ± .03   | 1.77 ± .13    |
| GPRP              | 1.38 ± .16    | 0.98 ± .03   | 0.85 ± .08   | 0.79 ± .02    |
| GPRP-amide        | 0.65 ± .02    | 0.49 ± .02   | 0.44 ± .01   | 0.80 ± .01    |
| Fib. Recept. Pept.| 0.56 ± .02    | 0.42 ± .01   | 0.38 ± .02   | 0.73 ± .08    |
| FPA               | 0.61 ± .05    | 0.43 ± .03   | 0.31 ± .005  | 0.69 ± .02    |
| FPB               | 0.67 ± .04    | 0.47 ± .02   | 0.41 ± .04   | 0.80 ± .02    |

Table 9 illustrates an analysis of the binding of biotinylated amino acid sequence 17–28 of human fibrinogen Aα Chain (SAC[KBtn]) to RA synovial fibroblasts by Flow Cytometry. The biotinylated control peptide (KREE-SEQ ID NO:3) represents corresponding sequences derived from the B/beta chain of fibrinogen following removal of Fibrinopeptide B.

TABLE 9

GPRVVERHQSAC[KBtn] = SAC [KBtn]
GHRPLDKKREE[KBtn] = KREE[KBtn] = control peptide

| RA #16      |         | % Cells Positive | Mean Fluorescent Channel |
|-------------|---------|------------------|--------------------------|
| Avidin-FITC |         | 3.6              | 13.71                    |
| SAC [KBtn]  | 200 ug  | 80.0             | 125.1                    |
| SAC [KBtn]  | 100 ug  | 86.3             | 257.9                    |
| KREE [KBtn] | 100 ug  | 10.6             | 20.37                    |

Table 10 illustrates Flow Cytometry Analysis of SAC Competition Assay.

TABLE 10

Synovial cells were incubated with unlabeled Fgn(2.5 mg), SAC(2.5 mg)
or GPRP (SEQ ID NO:2) (2.5 mg) for 3 hours followed by labeled
SAC[KBtn] for 1 hour

|                              | Mean  |
|------------------------------|-------|
| AVIDIN-FITC                  | 20.16 |
| SAC[KBtn], Avidin-FITC       | 51.20 |
| Fgn: SAC[KBtn], Avidin-FITC  | 21.63 |
| SAC: SAC[KBtn], Avidin-FITC  | 36.30 |
| GPRP: SAC[KBtn], Avidin-FITC | 33.58 |

These data suggest that unlabeled fibrin, unlabeled GPRVVERHQSAC (SAC) (SEQ ID NO: 4) and unlabeled GPRP (SEQ ID NO:2) can compete with biotin-labeled SAC for binding to human synovial fibroblasts. This competition further suggests that the labeled peptide competitively binds to a specific cell surface receptor of synovial cells. Thus, labeled peptide could facilitate the isolation, identification and characterization of its receptor, through standard immunological techniques such as immunohistochemistry, flow cytometry and immunoprecipitation.

The data collected thus far leads me to believe that there exist on the surface of human synovial cells, a receptor that can be stimulated when fibrinogenesis is ocurring in the synovial joint. The ligand for this receptor is created when newly exposed amino acid sequences become available due to Fibrinopeptide A release from the precursor fibrinogen. This newly exposed "knob" has two options: 1) it can bind to fibrinogen gamma chains thereby promoting cross-links and the formation of fibrin clots, or 2) given the right environment (synovial cells bearing the correct receptor) can also act as ligand for these cellular receptors. Binding of the ligand stimulates intracellular signaling mechanisms some of which require NF-kappa B and results in the simultaneous expression and production of pro-inflammatory mediators, such as an array of adhesion molecules and chemotactic cytokines.

Further research is contemplated to determine what further activities synovial FB might produce under the influence of this ligand (IL-1, chemoattractant IL-16, MCP-1, prostaglandin production, matrix metalloprotease production, and collagenase-1 and cathepsin production, for example). It is believed that in vivo, fibrin-induced activation of synovial FB results in the induction of a phenotypic "Pro-Inflammatory FB" leading to the recruitment, activation, attachment and retention of lymphocytes, all of which occur to a tremendous degree in the chronically inflamed rheumatoid joint. It is well known that the recruitment and attachment of lymphocytes to synovial FB results in further amplification of inflammation. Most recent therapies directed at biologically alleviating inflammation in the rheumatoid joint have focused on inhibiting one or another facets of the inflammatory response, i.e., using anti-ICAM-1 monoclonals, monoclonal antibodies or engineered proteins directed against TNF, etc., and are very costly.

A recent review by Lorenz, et. al (Reference 27) discusses the advantages and disadvantages of current and emerging RA therapies and describes further efforts to reduce inflammation via antibodies to specific cytokines. It is becoming apparent that studies targeting a single biological entity at a time are being replaced by studies in which they are combined with more traditional anti-inflammatory medications. Also contained in this review is a discussion of emerging results for targeting the membrane urokinase-type plasminogen activator of human synoviocytes. My findings could advance such approaches. A double blind clinical trial of stanozolol (enhances both systemic and intra-articular fibrinolytic activity) in RA patients (Reference 29) resulted in clinical benefit, i.e., decrease in erythrocyte sedimentation rate, improvement in articular index, decreased duration of morning stiffness, decrease in pain, and decreased plasma fibrinogen concentrations. It was believed that the clinical improvement likely could have been due to the induced reduction of synovial fibrin.

It is believed that once we more fully understand the effects of the peptide of the invention on synovial FB, as compared with less specialized FB found elsewhere in the body, a modification thereof, including the amide form, could be used as a binding, but non-signalling ligand, which would specifically target synovial fibroblasts, and thereby prevent the natural ligand from provoking the fibroblasts towards the pro-inflammatory phenotype. Since it is known that procoagulant activity occurs at a heightened level in a rheumatoid joint, this would represent an important approach to subduing the inflammatory component. It may also answer the question of exactly how fibrinogenesis promotes inflammation—a fact long known to be true, but its mechanism still unknown.

I am not aware if the reported activities of all of the modified peptides that have been created in studies of fibrinogen polymerization, have any bearing on our observations. There is no evidence to suggest that the gamma chain "hole" is the same size or sequence as our putative receptor on synovial cells. Modified peptides which reportedly do not bind the gamma chain "hole" may still bind to this receptor and any peptide derivatives (previously known to inhibit fibrin polymerization or not) would have to be re-tested using our cell system.

Looking in a new direction, extravascular fibrin deposition is also frequently observed in association with neoplastic tissues in vivo. Many clinical and experimental findings (References 21–23) support the hypothesis that fibrin facilitates tumor growth and metastasis, although the mechanisms are not yet known. In a recent study of fibrin deposition in head and neck tumors (Reference 24), there was evidence of in situ thrombin activation and fibrin formation, and it was noted that the fibrin deposition was almost exclusively localized to the connective tissue compartment immediately surrounding the tumors. In 10/25 laryngeal and 4/9 hypopharyngeal cancers, characteristic fibrin accumulation was seen around tumor cell nodules, at the interface of connective tissue and tumorous parenchyma. Tumor cell clusters were observed embedded within connective tissue "soaked with fibrin". Fibrin was not detected in the histologically normal part of tissue surrounding the squamous cell carcinomas. We look to culture connective tissue fibroblasts originating from these areas surrounding the tumors with the expectation that GPRP (SEQ ID NO:2) or other peptides like it may induce a release of factors from these specialized FB which in turn would have a "feeder", or pro-cancerous effect on the tumor cells.

The present invention also includes therapeutic or pharmaceutical compositions comprising a peptide or a peptide derivative of the invention in a form which can be combined with or in combination with a pharmaceutically acceptable carrier for any appropriate manner for administration, including, for example, oral, nasal, intravenous or intramuscular administration. Appropriate dosages, duration and frequency of administration would be determined by known factors, such as the condition of the patient, the type and severity of the disease and the method of administration. The term "carrier" includes a diluent, adjuvant, excipient, or vehicle with which the peptide is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The therapeutic compositions, if desired, can also contain minor amounts of wetting or emulsifying agents, or pH buffering agents. These compositions can take the form of solutions, suspensions, emulsion, tablets, capsules, powders, sustained-release formulations and the like. The composition can be formulated with traditional binders and carriers such as triglycerides. Examples of suitable pharmaceutical carriers are described in "Remington's Pharmaceutical Sciences" by E. W. Martin. Such compositions contain a therapeutically effective amount of the therapeutic composition, together with a suitable amount of carrier so as to provide the form for proper administration to the patient. The formulation should suit the mode of administration.

The composition may be formulated in accordance with routine procedures as a pharmaceutical composition adapted for local injection administration to human beings. Typically, compositions for local injection administration are solutions in sterile isotonic aqueous buffer. Where necessary, the composition may also include a solubilizing agent and a local anesthetic, such as lidocaine to ease pain at the site of the injection. Generally, the ingredients are supplied either separately or mixed together in unit dosage form, for example, as a dry lyophilized powder or water free concentrate in a hermetically sealed container, such as an ampoule or sachette indicating the quantity of active agent. Where the composition is administered by injection, an ampoule of sterile water for injection or saline can be provided so that the ingredients may be mixed prior to administration.

The therapeutic or pharmaceutical compositions of the invention can be formulated as neutral or salt forms. Pharmaceutically acceptable salts, include those formed with free amino groups, such as those derived from hydrochloric, phosphoric, acetic, oxalic, tartaric acids, etc., and those formed with free carboxyl groups, such as those derived from sodium, potassium, ammonium, calcium, ferric hydroxides, isopropylamine, triethylamine, 2-ethylamino ethanol, histidine, procaine, etc.

The present invention also provides for the modification of the peptide or peptide derivatives such that it is more stable once administered to a subject, i.e., once administered it has a longer time period of effectiveness as compared to unmodified peptide. Such modifications are well known to those of skill in the art, e.g., polyethylene glycol derivatization (PEGylation), microencapsulation, etc.

While this invention has been described as having preferred sequences, ranges, steps, materials, or designs, it is understood that it includes further modifications, variations, uses and/or adaptations thereof following in general the principle of the invention, and including such departures from the present disclosure as those come within the known or customary practice in the art to which the invention pertains, and as may be applied to the central features hereinbeforesefforth, and fall within the scope of the invention and of the limits of the appended claims. It is further understood that the present invention is not limited to the claims appended hereto.

References

1. Colvin R B, Johnson R A, Mihm M C, and Dvorak H F. *Role of the Clotting System in Cell-Mediated Hypersensitivity.* J Exp Med 1973, 138:686–698.
2. Accini L, Dixon F J. *Degenerative Vascular Disease and Myocardial Infarction in Mice with Lupus-like Syndrome.* Am J. Pathol 1979, 96:477–492.
3. Wood R M, Bick M W. *The Effect of Heparin on the Ocular Tuberculin Reaction.* Arch Opthamol 1959, 61:709–711.
4. Cohen S B, Benacerraf B, McCluskey R T, Ovary Z. *Effects of Anticoagulants on Delayed Hypersensitivity Reaction.* J Immunol 1967, 98:351–358.
5. Colvin R B, Dvorak H F. *Role of the Clotting System in Cell-Mediated Hypersensitivity II. Kinetics of Fibrinogen/fibrin Accumulation and Vascular Permeability Changes in Tuberculin and Cutaneous Basophil Hypersensitivity Reactions.* J Immunol 1975, 114:377–387.
6. Edwards R L, and Rickles F R. *Delayed Hypersensitivity in Man: Effects of Systemic Anticoagulation.* Science 1978, 200:541–543.

7. Colvin R B, Mosesson M W, Dvorak H F. *Delayed Type Hypersensitivity Skin Reactions in Congenital Afibrinogenemia Lack Fibrin Deposition and Induration.* J Clin Invest 1979, 63:1302–1306.
8. Malik A B, Johnson A, Tahamont M V. *Mechanisms of Lung Vascular Injury After Intravascular Coagulation.* Ann NY Acad Sci 1982, 384:213–234.
9. Kay A B, Pepper D S, McKenzie R. *The Identification of Fibrinopeptide B as a Chemotactic Agent Derived from Human Fibrinogen.* Br J Hematol 1974, 27:669–677.
10. Richardson D L, Pepper D S, Kay A B. *Chemotaxis for Human Monocytes by Fibrinogen Derived Peptides.* Br J Hematol 1976, 32:507–513.
11. Sueishi K, Nanno S, Tanaka K. *Permeability Enhancing and Chemotactic Activities of Lower Molecular Weight Degradation Products of Human Fibrinogen.* Thromb Haemost 1981, 45:90–94.
12. Rowland F, Donovan M, Gillies C, O'Rourke J, Kreutzer D L. *Fibrin: Mediator of In Vivo and In Vitro Injury and Inflammation.* Curr Eye Res 1985, 4:537–553.
13. Saxne T, Lecander I, Geborek P. *Plasminogen Activators and Plasminogen Activator Inhibitors in Synovial Fluid Difference Between Inflammatory Joint Disorders and Osteoarthritis.* J Rheumatol 1993, 20:91–96.
14. Kikuchi H, Tanaka S, Matsuo O. *Plasminogen Activator in Synovial Fluid from Patients with Rheumatoid Arthritis.* J Rheumatol 1987, 14:439–445.
15. Kummer J A, Abbink J J, De Boer J P, Roem D, Nieuwenhuys E J, Kamp A M, Swaak T J G, Hack C E. *Analysis of Intraarticular Fibrinolytic Pathways in Patients with Inflammatory and Noninflammatory Joint Diseases.* Arthritis Rheum 1992, 35:884–893.
16. Belch J J F, McArdle B, Madhok R. *Decreased Plasma Fibrinolysis in Patients with Rheumatoid Arthritis.* Ann Rheum Dis 1984, 43:774–777.
17. Dahlquist S R, Jonsson S W, Ranby M. *Fibrinolytic Components in Synovial Fluid of Destructive and Non-Destructive Arthritis.* Arthritis Rheum 1994, 37:S248.
18. Herrick A L, Illingworth K, Blann A, Hollis S, Jayson M I V. *Von Willebrand Factor, Thromboxane, B-Thromboglobulin and Markers of Fibrinolysis in Primary Raynaud's Phenomenon and Systemic Sclerosis.* Arthritis Rheum 1994, 37:S259.
19. Qi J, Kreutzer D L, Piela-Smith T H. *Fibrin Induction of ICAM-1 Expression in Human Vascular Endothelial Cells.* J Immunol 1997, 158:1880–1886.
20. Kawasaki K, Hirase K, Masanori M, Tsuji T, Iwamoto, M. *Amino Acids and Peptides XVI. Synthesis of N-terminal Tetrapeptide Analogs of Fibrin a Chain and Their Inhibitory Effects on Fibronogen/fibrin Clotting.* 1992. Chem Pharm Bull 40:3253–3260.
21. Clifton E E, Grossi C E. *The Rationale of Anticoagulants in the Treatment of Cancer.* J Med 1974, 5:107–113.
22. Peterson H I. *Fibrinolysis and Antifibrinolytic Drugs in the Growth and Spread of Tumors.* Cancer Treat Rev 1977, 4:213–217.
23. Zacharski L R, Henderson W G, Rickles F R, Forman W B, Cornell C J Jr, Forcier R J, Edwards R, Headley E, Kim S H, O'Donnell J R, O'Dell R, Tornyos K, Kwaan H C. *Effect of Warfarin on Survival in Small Cell Carcinoma of the Lung.* JAMA 1981, 245:831–835.
24. Bardos H, Juhasz A, Repassy G, Adany R. *Fibrin Deposition in Squamous Cell Carcinomas of the Larynx and Hypopharynx.* Thromb Haemost 1998, 80:767–772.
25. Laudano A P, Doolittle R F. *Studies on Synthetic Peptides That Bind to Fibrinogen and Prevent Fibrin Polymerization. Structural Requirements, Number of Binding Sites, and Species Differences.* 1980, Biochemistry 19:1013–1019.
26. Shreck R, Meier B, Manne D, Droge W, Bauerte P A. *Dithiocarbamate as Potent Inhibitors of Nuclear Factor kB in intact Cells.* J Exp Med 1992, 175:1181–1194.
27. Lorenz H-M, Kalden J R. *Biologic Agents in the Treatment of Inflammatory Rheumatic Diseases.* 1999, Curr Opin Rheumatol 11:179–184.
28. Rothchild, B M, Thompson, L D, Pifer D D, Chesney C M. *Perturbation of Protease Inhibitors and Substrates in Inflammatory Arthritis.* Semin Thromb Hemostasis 1985, 11:394–404.
29. Belch J J F, Madhok R, McArdle B, McLaughlin K, Kluft C, Forbes C D, Sturrock R D. *The Effect of Increasing Fibrinolysis in Patients with Rheumatoid Arthritis: A Double Blind Study of Stanozolol.* Q J Med 1986, 58:19–27.

---

What is claimed is:

1. A method of inducing pro-inflammatory effects in synovial cells, comprising:

exposing a plurality of synovial cells to a peptide comprising an amino acid sequence set forth in SEQ ID NO: 2; and culturing the exposed cells and obtaining or/and assessing the result of inducing pro-inflammatory effect in the synovial cells.

2. The method of claim 1, wherein the peptide has pro-inflammatory effects on human synovial cells.

3. The method of claim 1, wherein the peptide induces expression of cell adhesion molecules in human synovial cells.

4. The method of claim 1, wherein the peptide has pro-inflammatory effects on synovial cells of a rheumatoid joint of a patient.

* * * * *